United States Patent [19]
Smith

[11] Patent Number: 6,094,472
[45] Date of Patent: Jul. 25, 2000

[54] X-RAY BACKSCATTER IMAGING SYSTEM INCLUDING MOVING BODY TRACKING ASSEMBLY

[75] Inventor: Steven W. Smith, Poway, Calif.

[73] Assignee: Rapiscan Security Products, Inc., Long Beach, Calif.

[21] Appl. No.: 09/060,009

[22] Filed: Apr. 14, 1998

[51] Int. Cl.[7] .................................................. G01N 23/10
[52] U.S. Cl. .................................. 378/86; 378/87; 378/88
[58] Field of Search .............................. 378/57, 86, 87, 378/88

[56] References Cited

U.S. PATENT DOCUMENTS

| Re. 28,544 | 9/1975 | Stein et al. | 250/369 |
|---|---|---|---|
| 3,780,291 | 12/1973 | Stein et al. | 250/363 |
| 3,790,799 | 2/1974 | Stein et al. | 250/363 |
| 4,031,545 | 6/1977 | Stein et al. | 358/108 |
| 4,228,353 | 10/1980 | Johnson | 250/356 |

(List continued on next page.)

FOREIGN PATENT DOCUMENTS

| 92/02892 | 2/1992 | WIPO | G06F 15/52 |

OTHER PUBLICATIONS

Stein, et al., "Flying Spot X–Ray Imaging Systems", Jul. 1972, American Science & Engineering, Inc., Cambridge, MA, pp. 137–142, Jul. 1972.

Arline Passenger Security Screening, Passenger Screening Technologies, pp. 13–21 (No Date).

American Science & Engineering Annual Report 1994, pp. 1–29.

American Science & Engineering Bodysearch, Micro–Dose Z–Ray Inspection System Specifications (No Date).

American Science & Engineering Bodysearch, Late 1991, First Known Brocure.

American Science & Engineering Bodysearch, Apr. 28, 1992, Second Known Brocure.

American Science & Engineering Bodysearch, Contraband Detection System, Late 1994, Third Known Brocure, Late 1994.

American Science & Engineering "Micro–Dose X–Ray Inspection System", Jun. 1987.

Ashley, Steven, "Airport X–Ray Spots Invisible Weapons", Popular Science, May 1986, p.38.

Bossi, et al., "Backscatter X–Ray Imaging", Materials Evaluation,46,Oct. 1998, pp. 1462–1467.

Discover, "Zee Secret Eez Zee Z's ", May 1986, vol. 7, No. 5.

Tracy, Eleanor Johnson, "A New X–Ray Scanner to Hinder Hijackers", Apr. 1986, Fortune Technology.

(List continued on next page.)

*Primary Examiner*—David P. Porta
*Assistant Examiner*—Drew A. Dunn
*Attorney, Agent, or Firm*—D'Alessandro & Ritchie

[57] ABSTRACT

A pencil beam of X-rays is scanned over the surfaces of the body of a person being examined as the person walks through the scanning apparatus. Specifically, a tracking assembly is employed to rotate the scanning plane through a tracking angle and in a direction progressing from the entrance to the exit of the portal, through which the person passes, in order to substantially track the person or body as it moves with respect to the system from the entrance to the exit X-rays that are scattered or reflected from the subject's body are detected by a detector assembly. The signal produced by this scattered X-ray detector in then used to modulate an image display device to produce an image of the subject and any concealed objects carried by the subject. The detector assembly is constructed in a configuration to automatically and uniformly enhance the image edges of low atomic number (low Z) concealed objects to facilitate their detection. A storage means is provided by which previously acquired images can be compared with the present image for analyzing variances in and similarities with the present image, and provides means for creating a generic representation of the body being examined while suppressing anatomical features of the subject to minimize invasion of the subject's privacy.

83 Claims, 12 Drawing Sheets

U.S. PATENT DOCUMENTS

| | | | |
|---|---|---|---|
| 4,242,583 | 12/1980 | Annis et al. | 250/358 |
| 4,242,588 | 12/1980 | Silk et al. | 250/492 A |
| 4,260,898 | 4/1981 | Annis | 250/505 |
| 4,342,914 | 8/1982 | Bjorkholm | 378/99 |
| 4,366,382 | 12/1982 | Kotowski | 378/57 |
| 4,366,576 | 12/1982 | Annis | 378/146 |
| 4,414,682 | 11/1983 | Annis et al. | 378/146 |
| 4,472,822 | 9/1984 | Swift | 378/10 |
| 4,503,332 | 3/1985 | Annis | 250/366 |
| 4,549,307 | 10/1985 | Macovski | 278/145 |
| 4,598,415 | 7/1986 | Luccio et al. | 378/119 |
| 4,768,214 | 8/1988 | Bjorkholm | 378/87 |
| 4,799,247 | 1/1989 | Annis et al. | 378/87 |
| 4,807,637 | 2/1989 | Bjorkholm | 128/664 |
| 4,809,312 | 2/1989 | Annis | 378/146 |
| 4,819,256 | 4/1989 | Annis et al. | 378/87 |
| 4,825,454 | 4/1989 | Annis et al. | 378/87 |
| 4,839,913 | 6/1989 | Annis et al. | 378/44 |
| 4,845,769 | 7/1989 | Burstein et al. | 378/58 |
| 4,864,142 | 9/1989 | Gomberg | 250/390 |
| 4,890,310 | 12/1989 | Umetani et al. | 378/82 |
| 4,893,015 | 1/1990 | Kubierschkey et al. | 250/369 |
| 4,899,283 | 2/1990 | Annis | 364/413.15 |
| 4,974,247 | 11/1990 | Friddell | 378/90 |
| 5,007,072 | 4/1991 | Jenkins et al. | 378/88 |
| 5,022,062 | 6/1991 | Annis | 378/86 |
| 5,044,002 | 8/1991 | Stein | 378/54 |
| 5,115,459 | 5/1992 | Bertozzi | 378/88 |
| 5,127,030 | 6/1992 | Annis et al. | 378/150 |
| 5,179,581 | 1/1993 | Annis | 378/57 |
| 5,181,234 | 1/1993 | Smith | 378/87 |
| 5,182,764 | 1/1993 | Peschmann et al. | 378/57 |
| 5,224,144 | 6/1993 | Annis | 378/146 |
| 5,247,561 | 9/1993 | Kotowski | 378/87 |
| 5,253,283 | 10/1993 | Annis et al. | 378/100 |
| 5,313,511 | 5/1994 | Annis et al. | 378/87 |
| 5,367,552 | 11/1994 | Peschmann | 378/57 |
| 5,420,905 | 5/1995 | Bertozzi | 378/88 |
| 5,463,224 | 10/1995 | Burstein et al. | 250/366 |
| 5,483,569 | 1/1996 | Annis | 378/87 |
| 5,600,700 | 2/1997 | Krug et al. | 378/57 |
| 5,602,893 | 2/1997 | Harding | 378/86 |
| 5,642,394 | 6/1997 | Rothschild | 378/57 |

OTHER PUBLICATIONS

Ellenbogen, Mike, "Checking in with New Bomb Detection Strategies" (No Date/No pp.).

Gregory, William H., "Medical X–Ray Measuring Device Finds Use in Explosive Detection", Apr. 28, 1986, vol. 124, No. 17, Aviation Week & Space Technology, p. 31.

Airline Passenger Security Screening, Health Effects, Paes 28–33 No Date.

Secure 1000 Personnel Security Screening System Web Page No Date/No pp.

"Micro Dose Finds Objects Under Clothing", Security Intelligence Report, Monday Mar. 11, 1991, p. 3.

Thompson, Estes, "Security Detector Sees All", No Source, No Date No Pages.

Towe, et al. "X–Ray Compton Scatter Imaging Using a High Speed Flying Spot X–Ray Tube", IEEE Transactions on Biomedical Engineering, vol. BME–28, No. 10, Oct. 1981, pp. 717–721.

X-RAY BACKSCATTER IMAGING SYSTEM INCLUDING MOVING BODY TRACKING ASSEMBLY

This application is related to the subject matter of U.S. Pat. No. 5,181,234.

FIELD OF THE INVENTION

The invention relates generally to a walk-through detection system, and more specifically, to a system and method which use low dosage radiation for detection of concealed objects carried on the body of a person as he or she moves through a detection area.

BACKGROUND OF THE INVENTION

Security systems are presently limited in their ability to detect contraband, weapons, explosives, and other dangerous objects concealed under a person's clothing. Metal detectors and chemical sniffers are commonly used for the detection of large metal objects and some kinds of explosives, however, a wide range of dangerous objects exist that cannot be detected with these devices. Plastic and ceramic weapons developed by modern technology increase the types of non-metallic objects that security personnel are required to detect. The alternative of manual searching of subjects is slow, inconvenient, and would not be well tolerated by the general public, especially as a standard procedure in, for example, airports.

Radiation exposure is an important consideration in X-ray concealed object detection systems. The United States National Council on Radiation Protection (NCRP), in NCRP Report No. 91, "Recommendations on Limits for Exposure to Ionizing Radiation", 1987, addresses this issue. In this report, the NCRP states that a radiation exposure of less than 1000 microRem per year in excess of environmental levels is negligible, and efforts are not warranted at reducing the level further. Persons employed in high security or secured facilities, or those who frequently travel by airlines, may be subjected to many hundred security examinations per year. A yearly radiation exposure limit of 1000 microRem permits a single scan exposure within the range of 1 to 10 microRem for the general public. In accordance with the NCRP recommendations, radiation levels significantly higher than this present a non-trivial health risk.

Known prior art X-ray systems suggested for detecting objects concealed on persons have limitations in their design and method which prohibit them from achieving the low dose and high image quality which are prerequisites to commercial acceptance. For example, radiant energy imaging systems that detect concealed objects carried on a person or in a container scan pencil beam of X-rays through the subject's body where the beam is transmitted or absorbed depending upon the concealed object, if any. A detector is scanned vertically behind the subject to collect the transmitted X-rays. The X-ray tube potential for these systems is set at up to 150 Kilovolts and is specifically chosen to transmit X-rays through the person being examined. This technique requires the subject to be exposed to a substantial radiation dosage, especially if the subject is scanned often, e.g., a frequent flyer.

Flying spot scanning systems for baggage inspection, also known in the art, utilize X-ray-induced fluorescence to permit detection of concealed objects. Since fluorescence is dependent upon atomic number, each object emits a fluorescent radiation line which is unique to its atomic number Z. Scattered, transmitted and fluorescence signals are generated to distinguish objects from the background. The energy level of the source must be sufficient to produce a large number of X-rays, at a selected fluorescent radiation line, that escape the object. Thus, it may be necessary to expose the object to relatively high X-ray energy in order to detect certain materials, which would be unacceptable for personnel inspection systems.

Inspection systems which operate at low levels of radiation exposure are limited in precision by the small number of X-rays that can be directed against persons being searched. X-ray absorption and scattering further reduces the number of X-rays available to form an image of the person and any concealed objects. In prior art systems, this low number of detected X-rays has resulted in unacceptably poor image quality. In addition, these systems do not adequately detect plastics, ceramics, explosives, illicit drugs, and other non-metallic objects. One reason in particular is that these materials share the property of a relatively low atomic number (low Z). Low Z materials present a special problem in personnel inspection because of the difficulty in distinguishing the low Z object from the background of the subject's body which also has low Z.

Other baggage inspection systems known in the art include detectors for both transmitted and backscattered X-rays to independently produce signals from the same incident beam. The separate signals may then be used to enhance each other to increase the system's accuracy in recognizing low Z materials. Clearly, with the incident beam being of sufficient energy to provide both transmitted and backscattered signals, the X-ray energy must be relatively high, making such a system undesirable for personnel inspection. U.S. Pat. No. 5,181,234, assigned to the assignee of the present invention, relates to an X-ray inspection system.

It would be desirable to provide a walk-through X-ray inspection system that automatically scans an individual from a variety of angles to provide a thorough search of the individual for metals as well as low Z materials, but which does not expose the subject to radiation doses significantly higher than normal environmental radiation levels. It is to such a system that the present invention is directed.

SUMMARY OF THE INVENTION

It is an advantage of the present invention to provide an X-ray personnel detector which is capable of rapid inspection of persons to detect metals as well as low Z materials (plastics, ceramics and illicit drugs) which might be concealed beneath the person's clothing.

It is another advantage of the present invention to provide such rapid inspection at low levels of radiation which are safe under conditions requiring repeated use.

It is yet another advantage to provide a walk-through system that does not require a person being searched to stop in front of an apparatus and receive operator instructions on where and how to stand.

It is still another advantage to provide a system that can be configured as a portal for stand-alone use, or for use in combination with other walk-through devices such as metal detectors, and that can provide optional covert screening.

In an exemplary embodiment, the present invention is a walk-through, concealed object detection system which utilizes low level radiation doses to detect weapons and dangerous materials, regardless of whether they consist of metal or low Z materials. The system is configured to include a left side module and a right side module separated by a distance sufficiently wide to allow a person to walk between the two modules. A housing, which may include a ceiling, conceals the left side module and the right side module, forming a portal configuration. This configuration can accommodate a high throughput of people as compared to the prior art because each person being screened simply walks, or is moved, such as by a moving walkway, through the portal, and does not need to stop and turn his or her body as directed by a scanner system operator. In addition, the portal configuration of the preferred embodiment, with its relatively confined area, is easier to combine with other walk-through devices, including metal detectors, drug and explosives sniffers, and video cameras.

The X-ray backscatter imaging system of the preferred embodiment can be used in conjunction with other security devices as described above, as a stand alone device, or as a built-in system that forms, for example, a doorway into a room of a building. The system, employed in any of these configurations, may be operated as a covert scanning system. A person who is not aware of the scanning process cannot take countermeasures to defeat the system. There are many security systems that are currently being used that, similarly, do not alert persons of their existence. For example, security cameras and infrared beams may covertly record and track the movements of individuals. Covert scanning is particularly useful for searching officials and dignitaries who cannot be overtly searched for diplomatic reasons.

The prior art disclosed in the '234 patent requires three seconds to complete a scan, and, because this time frame is insufficient to "freeze" the walking motion, a scan of this length results in unacceptable shifted images and motion artifacts. A typical person may walk past a scanner at a speed of about one meter, or 40 inches, per second. Therefore, a 10 cm (four inch) maximum advancement, which has been determined to produce an acceptable scan image, equates to an entire body scan that must be completed in 0.1 seconds. The X-ray apparatus of the prior art utilizes a horizontal sweep to scan a horizontal "slice" of the subject's body. The X-ray beam sweeps in a horizontal motion by means of a mechanical collimator known in the prior art. The vertical component of the scan is accomplished by physically moving the assembly in the vertical direction to provide scan of horizontal "slices" along the height of the subject's body. This technique results in slow vertical scanning and fast horizontal scanning, and the resulting scan image is slanted either left or right from the top of the image to the base of the image due to the forward motion of the person being scanned.

The present invention overcomes these obstacles by "reversing" the vertical and horizontal scans as taught by the prior art. By utilizing a fast vertical scanning configuration in the preferred embodiment, acceptable images can be obtained when the scan duration for a complete scan is on the order of 0.3 seconds. The vertical component of the scan is accomplished using a chopper disk, having four slits, which is rotated at a high speed, e.g. over 2000 rpm, to create a narrow "pencil" beam of X-rays that is rapidly scanned in the vertical direction. In an exemplary embodiment, the chopper disk rotates at approximately 6000 rpm. An example of a chopper disk material that is suitable for high speed operation is a copper-tin-zinc alloy with 3–10 percent added lead. This material minimizes disk warping due to internal stresses caused by the high-speed rotation.

The horizontal component of the scan is achieved by employing a turntable-type apparatus to provide a simple rotation around a vertical axis. A rotating assembly overcomes the gravitational limitations of the prior art, and a complete vertical/horizontal scan from an single angle can be completed in the desired 0.3 seconds.

The image distortion associated with fast vertical scanning causes the image to be uniformly compressed or expanded in the horizontal direction. If the horizontal scanning motion is in the same direction as the direction in which the person is moving or walking, the acquired image of the person appears wider than in actual life. Similarly, if the horizontal scanning motion is in the opposite direction, the acquired image of the person appears thinner.

In the preferred embodiment, an X-ray source is included in the left side module and the right side module. The X-ray sources are movably positioned at a height corresponding to the mid to upper torso of a subject of average height. Each source is rapidly repositioned to obtain either a front or a rear view, and thus the system acquires four images from four different angles allowing all sides of a walking subject to be automatically searched. Other embodiments may contain additional X-ray sources staggered along the portal with each X-ray source positioned to obtain a different image. For example, four X-ray sources may be utilized to obtain four images including a front right scan, a front left scan, a rear right scan, and a rear left scan.

Each module of the preferred embodiment contains an array of fourteen detectors and the ceiling contains four detectors for a total of thirty two detectors for the entire assembly. The thirty-two detectors form a composite detector array that can be used to produce an image of the subject who is located at any of four possible scanning positions. Other embodiments may contain fewer or more detectors in each of the side modules and the ceiling. Also, the detector array may be located only in the side modules, with no detectors located in the ceiling.

As the subject enters the apparatus of the preferred embodiment, the X-ray source and detectors are activated by an operator or are automatically activated using triggering devices such as optical beams, pressure sensitive pads, or other motion detecting devices. The subject proceeds through the portal and is scanned from different angles by an X-ray source to his or her left and an X-ray source to his or her right. A thorough scan of each subject is accomplished by obtaining four views including a left front scan, a right front scan, a left rear scan, and a right rear scan in a sequence that is determined by the module configuration. The X-ray source of the modules are offset from the center of the module, so that when the modules are placed to face inward to form a portal, one X-ray source is closer to the entrance of the portal, and the opposing X-ray source is closer to the exit of the portal. This configuration facilitates a sequential scanning process as described below.

In the preferred embodiment, as the subject being scanned enters the portal, the left side module X-ray scanner, which is closest to the portal entrance and angled to face a front left side scan area located proximate to the entrance, performs a scan of the front left side of the person. The detector array of the left side module collects the reflected back-scattered X-rays, and produces electrical signals with values based upon the characteristics of the X-ray reflectance. The signals sent to the system processor generate a displayed image of the subject's left front side. The forward-advancing subject enters a front right side scan area, and is scanned by the scanner of the right side module. Upon completion of its first scan, the scanner of the left side module, which has rotated on the vertical axis to face a left rear scan area adjacent to the portal exit, is activated to complete a scan of the rear left side of the subject. Finally, as the subject nears the exit of the portal, the right side module, which has rotated to face a rear right side scan area, completes the scanning sequence with a scan of the rear right side of the subject being scanned.

In an alternate embodiment of the present invention, the subject is moved through the portal at a constant speed through utilization of a mechanical means, such as a moving walkway. A constant speed of progression of the subject being scanned is advantageous to maintain images of similar quality from person to person. This is clearly desirable because persons of different heights cover different distances in a single step, and therefore, a tall person may step beyond a scan area before the scan is complete. Also, people walk with different gaits, and a fast-walking person might walk through the scan area too-quickly, resulting in an incomplete scan. A constant speed of progression helps to assure that the person being scanned will be within a particular scan area for a predetermined time. The rotation of the X-ray sources about the vertical axis may be synchronized with the constant velocity to further improve the clarity of the image.

The embodiments of the present invention may be configured to utilize the image viewing concepts of the '234 patent of Smith, which teaches methods to obtain an indication of objects desired to be detected without requiring the operator to view an actual image of the subject's body. These methods include using a generic body outline or template to indicate relative location of concealed objects. Generic-type representations of the subject's body ease concerns related to a possibly objectionable invasion of privacy.

BRIEF DESCRIPTION OF THE DRAWINGS

Understanding of the present invention will be facilitated by consideration of the following detailed description of a preferred embodiment of the present invention, taken in conjunction with the accompanying drawings, in which like reference numerals refer to like parts and in which:

FIGS. 5a–5d illustrate the top views of a scan sequence, wherein FIG. 5a is front left scan, FIG. 5b is a front right scan, FIG. 5c is a rear left scan, and FIG. 5d is a rear right scan;

FIGS. 6a–6d illustrate front and rear scan images of a person walking, wherein FIG. 6a is a front left image, FIG. 6b is a front right image, FIG. 5c is a rear left image, and FIG. 5d is a rear right image;

FIGS. 7a–7b are top views of a scan sequence of a second embodiment of a portal configuration, wherein FIG. 7a shows a rear scan of a subject, and FIG. 7b shows a front scan of a subject;

FIGS. 9a–9e provide views of a fourth embodiment of an imaging system, wherein FIG. 9a is a perspective view of the portal, FIG. 9b is a top view of the portal, FIG. 9c is a front view of the portal, FIG. 9d is a right side view of the portal, and FIG. 9e is a perspective view of a subject being scanned;

DETAILED DESCRIPTION OF THE PREFERRED EMBODIMENT

Figure 1:
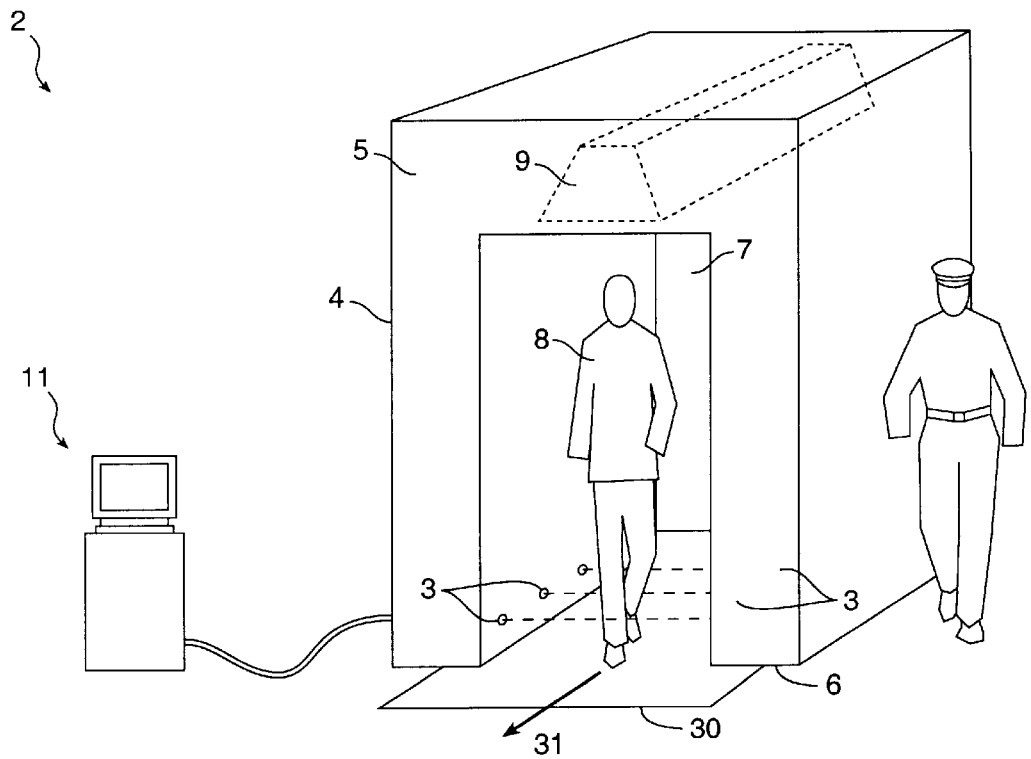
FIG. 1 is a perspective view of a portal structure containing the backscatter detection system of the preferred embodiment.
Figure 2:
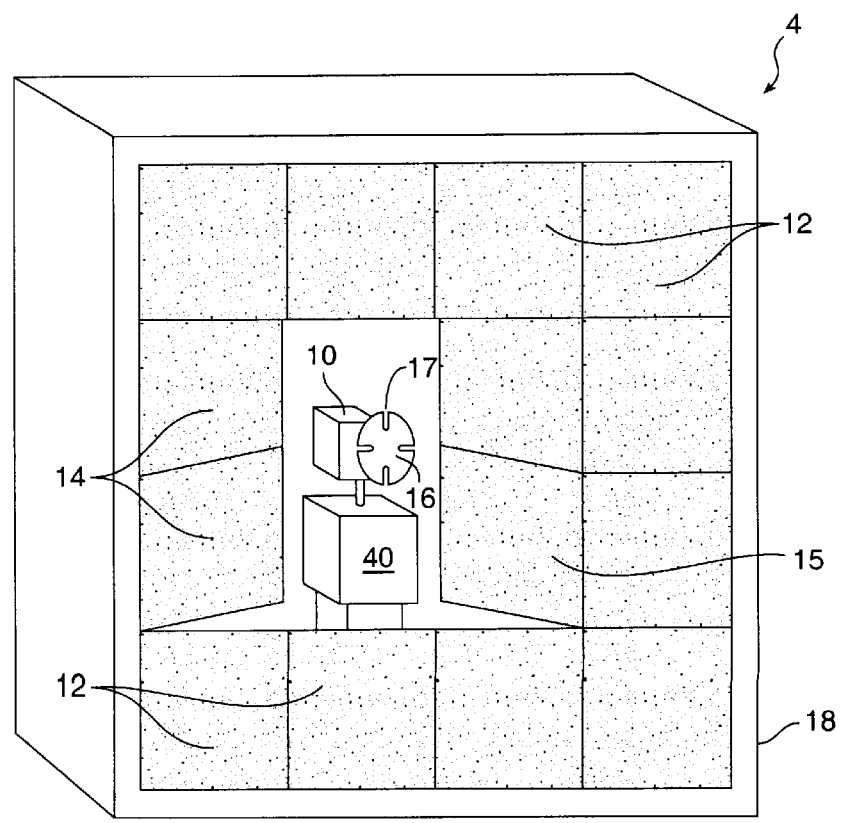
FIG. 2 is a perspective view of a right side module of the preferred embodiment.

FIG. 1 is a perspective view of a portal structure 2 of an X-ray backscatter imaging system of the preferred embodiment. The portal structure 2 encloses the elements of the X-ray imaging system and is designed to form a passageway 7 that extends through the imaging system from an entrance to an exit. The X-ray imaging system includes a left side module 6, a right side module 4, and an optional ceiling structure 5. Note that the use of the terms "right" and "left" are used according to the perspective of the person 8 being scanned as he or she moves through the passageway 7. However, the assignment of these descriptive terms are otherwise arbitrary, and the modules may be referred to in any of a number of ways including, for example, the "first" and "second" modules. A person 8 is scanned for concealed weapons or contraband as he or she walks, or is mechanically moved through the portal structure 2. A tracking means such as the rotational turntable 40 of FIG. 2, responds to motion detectors 3 which sense the movement of a person 8 with respect to the passageway 7. An X-ray scanning source such as 10 and 10' as shown in FIG. 2 is mounted on or affixed to the tracking means in order to track the person 8 as he or she moves through the passageway 7. The tracking means is not limited to the rotational turntable 40 of FIG. 2, but may also be sliding means, horizontal axis means, or other such means as are known in the art which could provide such tracking. In the preferred embodiment, the passageway 7 has a height and a width sufficient to allow a person 8 being scanned to walk through the passageway 7 while confining movement to within an acceptable range of the detectors. A typical dimension of a passageway 7 can be approximately 137 cm (4.5 feet) wide, 213 cm (7 feet) high, and 200 cm (6.5 feet) long. However, these dimensions may vary depending upon the installation location and the configuration of the elements of the X-ray imaging system that are contained within the portal structure 2. For example, in a second embodiment of the present invention as shown in FIG. 7, the portal is extended and includes a right and a left turn, which, as will be described below, facilitates scanning in a system that uses a limited number of scan areas. The back-scatter imaging system of the preferred embodiment may be a stand alone unit, or it may be used in a series or combination with other security devices. Therefore, it may be necessary to have a portal structure 2 that is configured to include a variety of security devices.

The portal structure 2 of the preferred embodiment is positioned upon a flooring 30. The flooring 30 may consist of the already-existing flooring of the chosen location for the imaging system, or alternatively, may consist of a specially-made flooring containing pressure sensitive electronics, or other similar devices, that trigger the operation of the X-ray imaging system. System triggering devices may also include electronics that are not associated with the flooring such as infra-red detectors, optical beams, ultrasonic sensors, microwave sensors, cameras with digital image analysis software. Such devices would ideally be located within or at the entrance of the portal 7. In other embodiments, the system may be triggered manually by an operator, or may be operated automatically based upon timing estimations of walking speeds of an average subject. The flooring 30 of other embodiments of the present invention may also contain detectors such as X-ray transmission detectors.

The triggering devices that commence operation of the system may also be used to interrupt the scanning process to prevent possible prolonged exposure to X-ray radiation in the event the subject stops walking, or a moving walkway is halted for some reason.

It is common for corridors to include moving walkways such as those found in major airports. The portal structure 2 may be designed to fit around a moving walkway, or alternatively, the portal structure 2 may be designed to include a flooring 30 with its own dedicated moving walkway. Mechanically moving walkways may be especially desirable to accommodate the physically challenged individual. Also, a moving walkway may be employed to control the speed of the person 8 being scanned as he or she moves through the portal structure 2.

Figure 3:
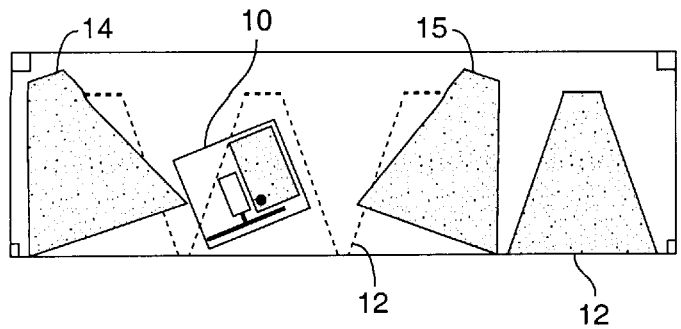
FIG. 3 is a top view of a right side module.
Figure 4:
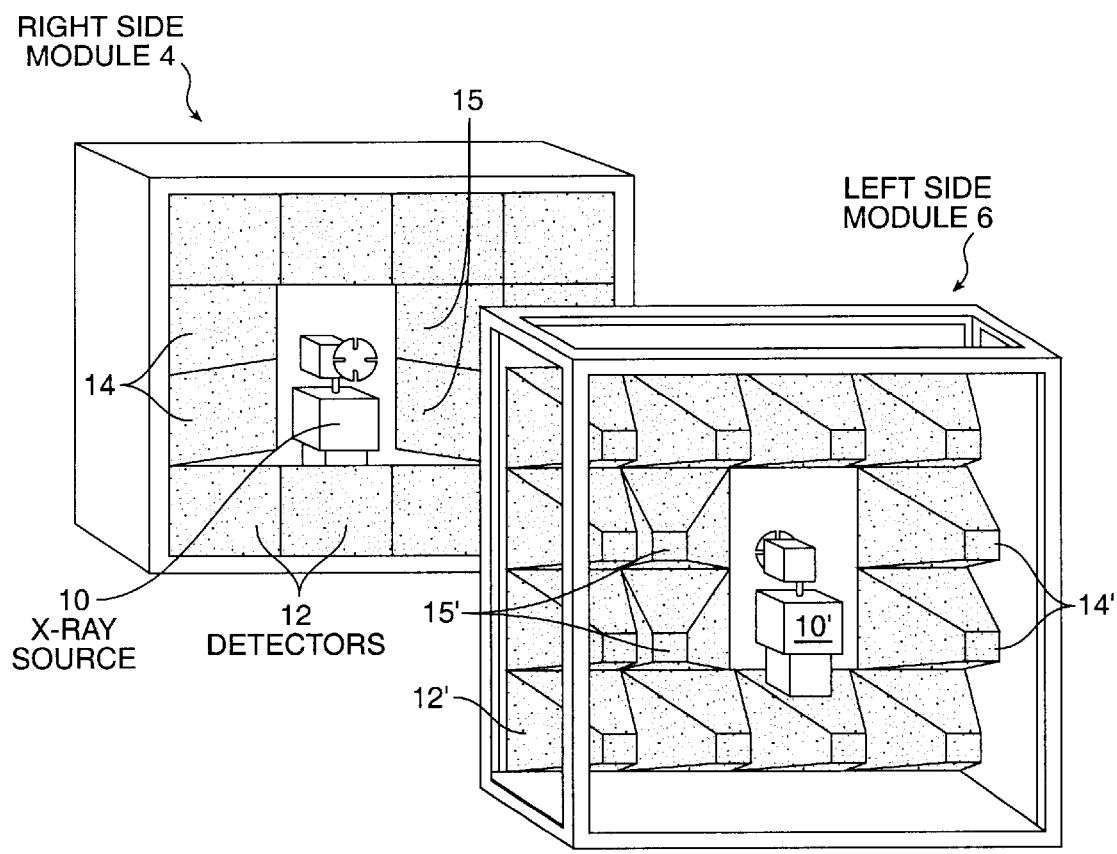
FIG. 4 is a perspective view of the left side module and the right side module.
Figure 10:
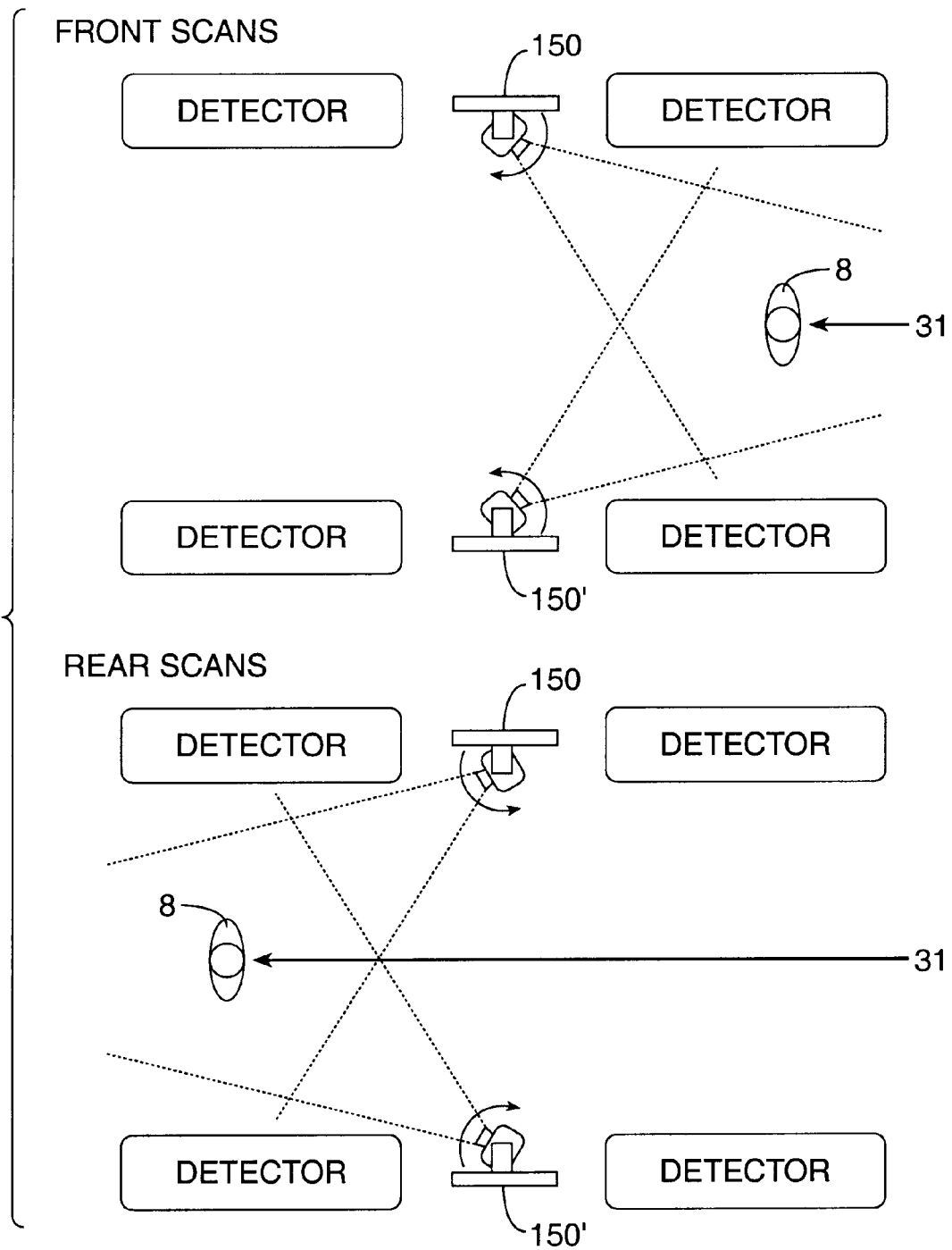
FIG. 10 illustrates an alternate placement of the X-ray sources.

The portal structure 2 of the X-ray backscatter imaging system of the preferred embodiment contains a right side module 4 and a left side module 6 as shown in FIG. 4. Each module 4, 6 of the exemplary embodiment is approximately 190 cm (75 inches) wide, 196 cm (77 inches) high, and 51 cm (20 inches) deep. These dimensions may vary for other embodiments of the invention depending upon the contents, location, and security application of the module. The configuration of each module 4, 6 is shown in more detail in the perspective drawing of a right side module 4 as shown in FIG. 2, and the top view of a right side module 4 as shown in FIG. 3. The right side module 4 of the preferred embodiment, which is interchangeable with the left side module 6, includes a frame 18 enclosing a rotatable X-ray source 10, and detectors 12, 14, 15. Interchangeability is not a necessity, but may be a desirable feature of the system for a variety of reasons including simplicity in the manufacturing of the modules 4, 6. In other embodiments, module 4 may be designed as a "mirror" version of module 6 such that the X-ray sources 150, 150' are located in directly opposing positions as illustrated in FIG. 10.

Also included with the system, as known in the prior art of the '234 patent of Smith, is the processor assembly 11 as shown in FIG. 1, which includes a computer processor for providing images to a monitor from the detected X-rays. The processor assembly 11 may be provided as part of the portal structure 2, or it may be remotely located utilizing appropriate cable connections.

FIG. 3 is a top view of the right side module 4 of the preferred embodiment, which illustrates the relative orientation of the detectors 12,14, 15. In the preferred embodiment, the detectors are as disclosed in the '234 patent, consisting of a light-tight enclosure, a fluorescent screen, and a photomultiplier tube. The detectors 12 are positioned such that their respective X-ray detection surfaces face the inside of the portal 7. The angled detectors 14, 15 of the preferred embodiment utilize the same technology as the detectors 12, the difference being in the physical positioning. The detectors 14, 15 are slightly angled with respect to the other detectors for the purpose of providing an unobstructed line of sight for the X-ray beams to strike the subject 8 being scanned. While the angling of these detectors 14, 15 does not substantially affect the imaging characteristics of the system, it does allow the X-ray source 10 and detectors 14, 15 to be placed in closer proximity. This, in turn, allows for the modules 4, 6 to have a minimal depth, such as the 51 cm (20 inches) of the preferred embodiment.

The prior art system of the '234 patent operated the X-ray source at 50 kV and 5 ma for a scan time of 3 seconds. To compensate for a shorter scan time of approximately 0.3 seconds per image, the exemplary embodiment increases the power to approximately 70 KV at 10 ma to achieve a greater X-ray intensity output. To further enhance the X-ray beam intensity, the diameter of the "pencil" beams is increased by a factor of approximately two by increasing the slit widths 17 on the chopper wheel 16 to a typical value of 15 mm. In an exemplary embodiment, a 20 cm (8 inch) diameter chopper 16 rotates at approximately 6000 rpm to rapidly scan a narrow "pencil" beam of X-rays in a vertical direction. The increased intensity combined with the shorter scan time maintain a safe radiation exposure of approximately 3 microRem.

The X-ray sources are located in the walls of the portal structure 2, and therefore, the measured dose will be greater near the sides of the passageway 7. However, because the dose is defined as the amount of energy being imparted into a certain volume, the total radiant energy being received by a subject 8 is approximately constant across a width of the passageway 7. The height of the X-ray sources within the module generally may be set to correspond to the mid-torso height of a relatively tall person, e.g., about six feet tall, so as to assure coverage of the fully body, head to toe. The vertical scan range should then be wide enough to cover taller subjects. For most subjects, these settings should locate the vertical center of the scan within a range around mid-torso.

To acquire an accurate image of a stationary person, the prior art of the '234 patent utilized a pixel spacing of 6 mm (0.25 in), such that a scan width of 120 pixels and a scan height of 348 pixels provided a 76 cm (30 inch) by 221 cm (87 inch) scan area. The exemplary embodiment of the present invention uses 9.5 mm (0.375 inch) pixel spacing resulting in a 128 pixel scan width and 256 pixel scan height that increases the scan area to 122 cm (48 inches) by 244 cm (96 inches). The increased scan areas 20, 22, 24, 26 provide larger windows for imaging persons that walk at different speeds through the portal 7. The larger pixel spacing and "pencil" beam diameter may diminish the spatial resolution of a preferred embodiment by about a factor of two compared to the system of the '234 patent. This represents the tradeoff for being able to scan moving subjects 8. As will be apparent, the pixel spacing, beam diameter, scan area, and scan rate can be varied depending upon factors such as the speed at which the subject 8 moves through the portal and the desired clarity of the scanned image. Walking speed can be controlled by instructing the subject 8 to decrease his or her walking speed, or by providing a moving walkway in which the subject 8 stands as he or she is moved (without walking) through the portal configuration 2 at a constant speed.

In the exemplary embodiment, the right side module 4 and the left side module 6 each contain an array of fourteen detectors, and the ceiling 5 contains a ceiling array 9 of four detectors for detecting backscattered X-rays from the subject 8 being scanned. (Note that the combination of the left and right detector arrays and the ceiling array 9 provides the overall system array.) These detectors must be capable of responding to a rapid pixel-to-pixel scanning rate. The persistence of the calcium tungstate ($CaWO_4$) flourescent screens used in the detectors of the prior art was approximately 40 microseconds, which was adequate for a pixel-to-pixel scanning rate of approximately 72 microseconds and allowed for a 348 by 120 pixel scan to be competed in 3 seconds. In the exemplary embodiment of the present invention, a 256 by 128 pixel area is completed in 0.3 seconds when each pixel is acquired in approximately 9 microseconds. Generally, in order to achieve the desired response, the persistence of the detectors should be less than 10 microseconds. Fluorescent screens suitable for the exemplary embodiment include barium lead sulfate ($BaPbSO_4$) with a persistence of 1 microsecond, or barium strontium sulfate ($BaSrSO_4$) with a persistence of 4 microseconds.

FIG. 4 is a perspective view of the left side scanning module 6 and the right side scanning module 4. The X-ray source 10 of the right side module 4 is located at a position towards the exit of the portal structure 2, and the X-ray source 10' of the left side module 6 is located at a position that is closer to the entrance of the portal structure 2. As shown in FIGS. 5a, 5b, 5c, and 5d, the offset positioning of the X-ray sources 10, 10' facilitates a sequential scan in the four scan areas 20, 22, 24, 26 as the person 8 is progressing forward along the line of movement 31.

Figure 5A:
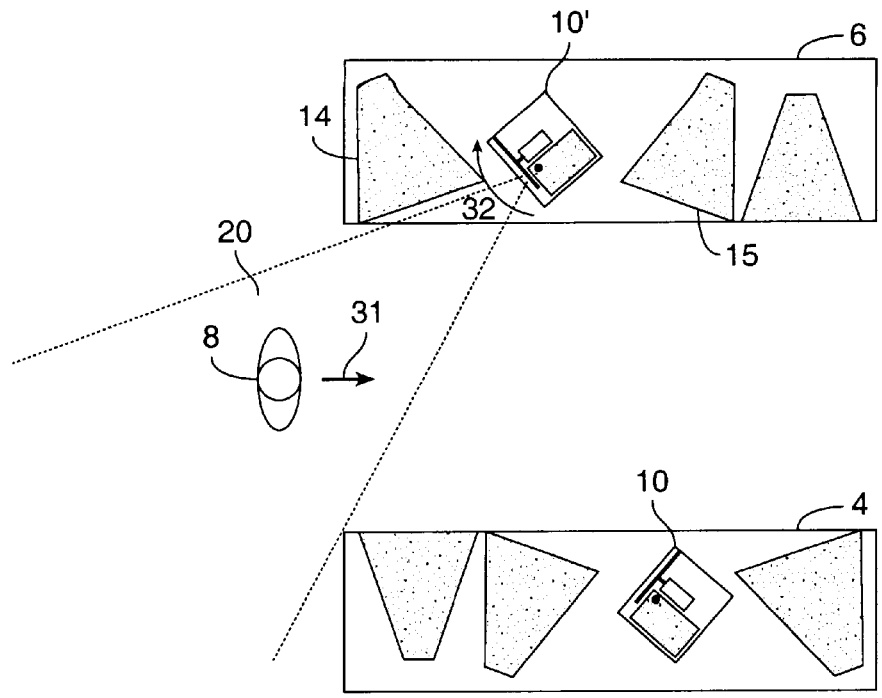

As illustrated in FIG. 5a of the preferred embodiment, the X-ray source 10' of the left side module 6 is activated first, and as the subject 8 enters the left side scan area 20, the X-ray source 10' provides a pencil beam of X-rays directed in a vertical motion along the height of the body of the subject 8 being examined. The X-ray source 10' rotates in a clockwise direction 32 to complete a horizontal scan across the width of the subject's body. X-rays that are scattered or reflected from the subject 8 are detected by the array of X-ray sensitive detectors that are positioned in the left side module 6, the right side module 4, and the ceiling 5. In an alternate mode of operation of the preferred embodiment, a selected subset of the detectors, for example, those located in the module of the active X-ray source, operate to detect the backscattered X-rays. The detectors of each module 4, 6 are positioned for substantially uniform X-ray detection on all sides of the incident X-ray beam. The electronic signal produced from the detector array, and synchronization signals from the X-ray source 10' are routed into a digital computer (not shown). The computer generates an image display of the subject's left front side on a monitor screen wherein the intensity at each point in the display corresponds to the relative intensity of the detected scattered X-rays.

Figure 5B:
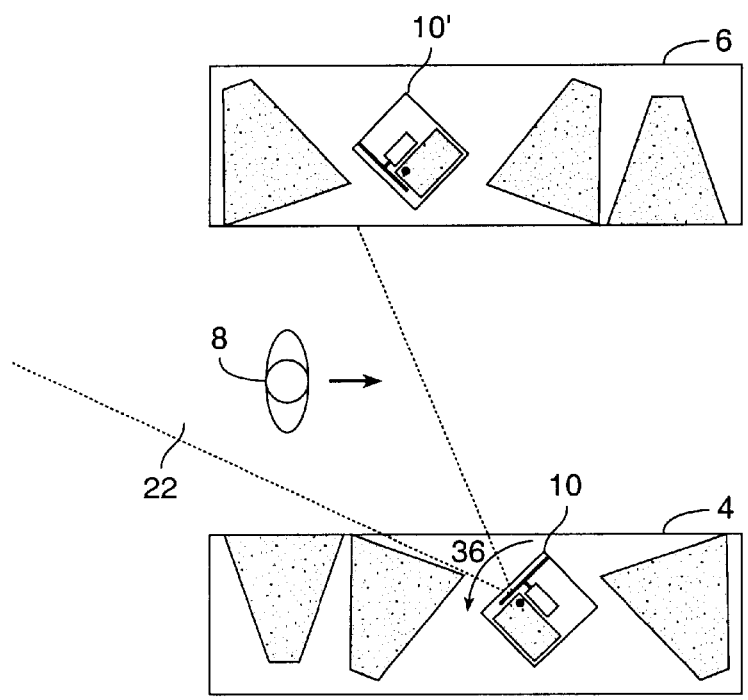
Figure 5C:
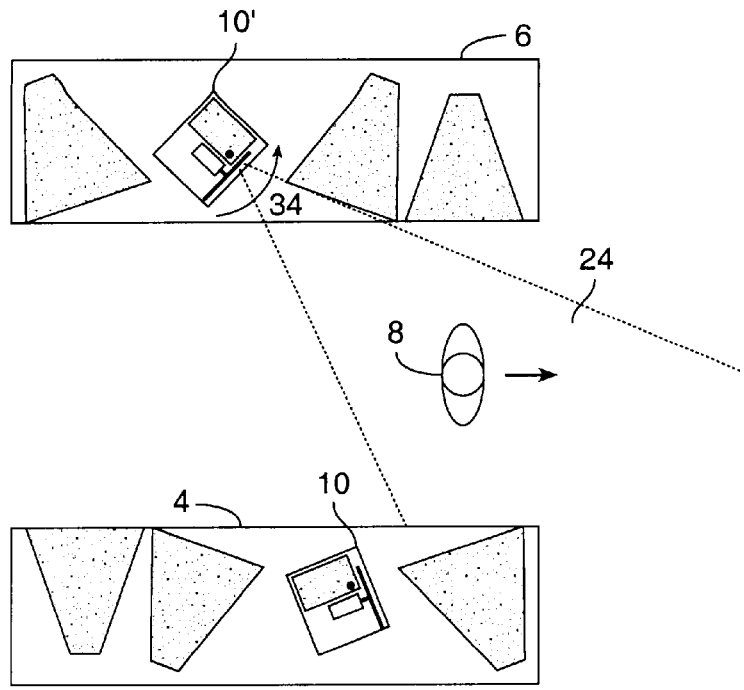
Figure 5D:
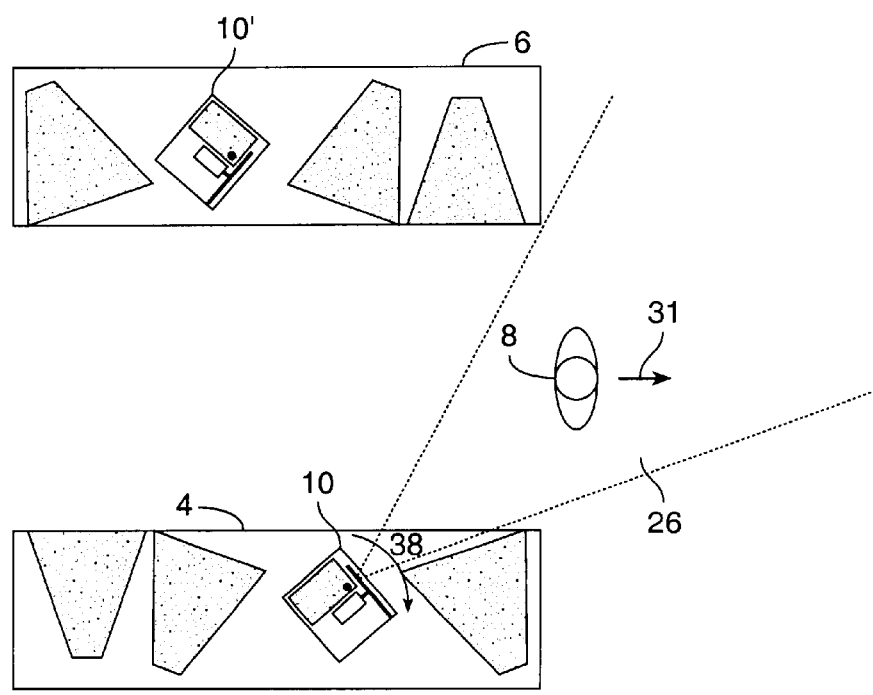

As the person 8 moves along a line of movement 31, the right side module 4 is activated as illustrated in FIG. 5b. The X-ray source 10 of the right side module 4 provides a vertical X-ray beam that is horizontally rotated counterclockwise 36 to produce a scan area 22. A detector array produces signals for images depicting the right front side of the subject's body. As the subject 8 proceeds into a left rear scan area 24 as illustrated in FIG. 5c, X-ray source 10', having rotated to a starting scan position directed towards scan area 24, scans the left rear side of the subject 8. The horizontal sweep of the subject 8 is accomplished by a counterclockwise rotation 34 of the X-ray source 10'. In FIG. 5d, a rear right side scan is the last scan of the sequence, and is accomplished by X-ray source 10 providing vertical beams in a clockwise sweep 38 of the rear right scan area 26.

Figure 6A:
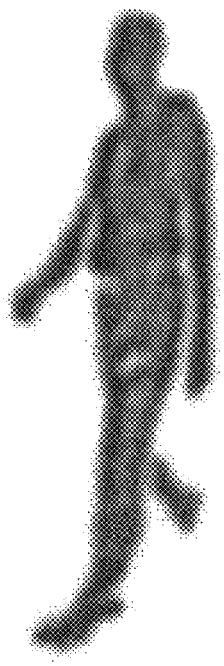
Figure 6B:
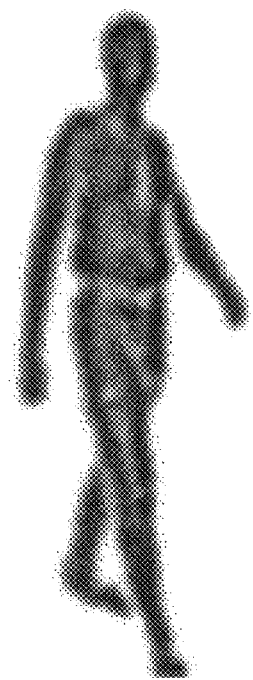
Figure 6C:
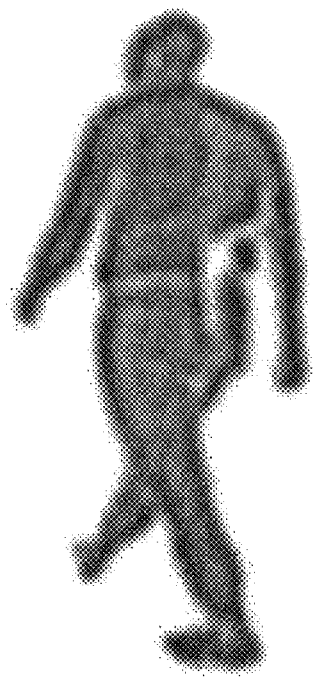
Figure 6D:
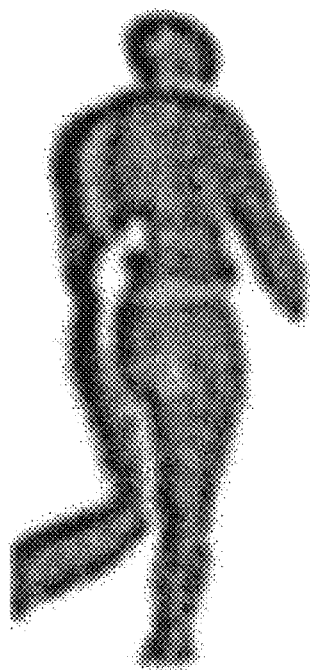

FIGS. 6a through 6d represent actual test images produced from the scans of FIGS. 5a through 5d respectively. The front side scans of FIGS. 5a and 5b show no indication of weapons. The dark areas within the front scan images of the subject indicate coins in the subject's pocket and a belt buckle. The left rear and right rear scan images of FIGS. 5c and 5d reveal a firearm tucked within the clothes of the subject. The front scan images of FIGS. 6a and 6b are nominally compressed in comparison to the rear scan images of FIGS. 6c and 6d. Compression of the images occurs as a result of horizontal scans that are in the opposite direction with respect to the line of movement 31. Similarly, expansion of the images occur when the horizontal scans sweep in a direction of the line of movement 31. It has been empirically determined that concealed objects can often be detected easier in the expanded images due to the larger image of the subject 8. However, it has also been empirically determined that compressed images have fewer motion artifacts.

Figure 7A:
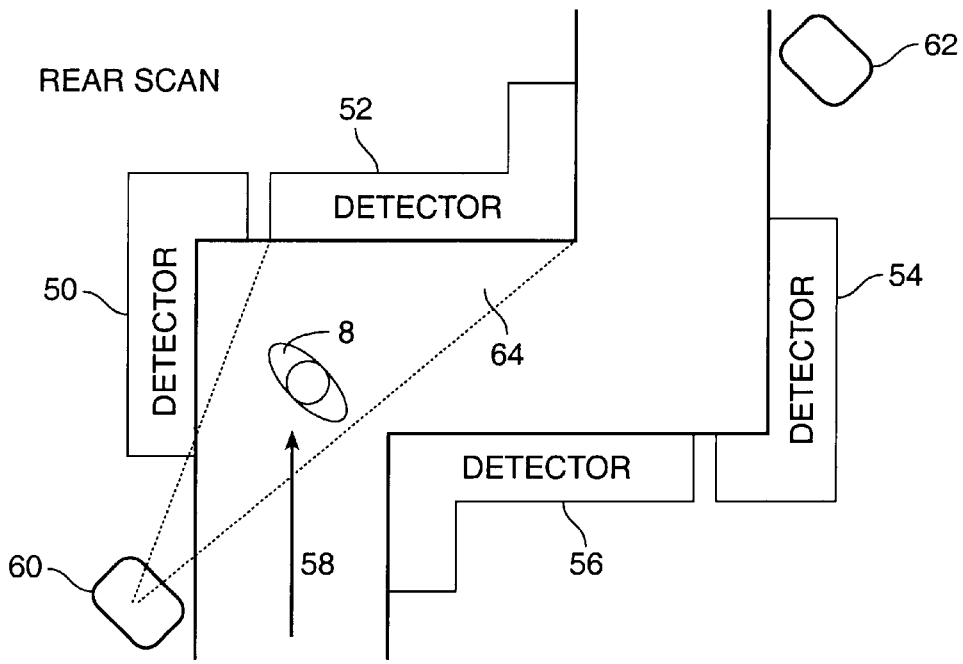
Figure 7B:
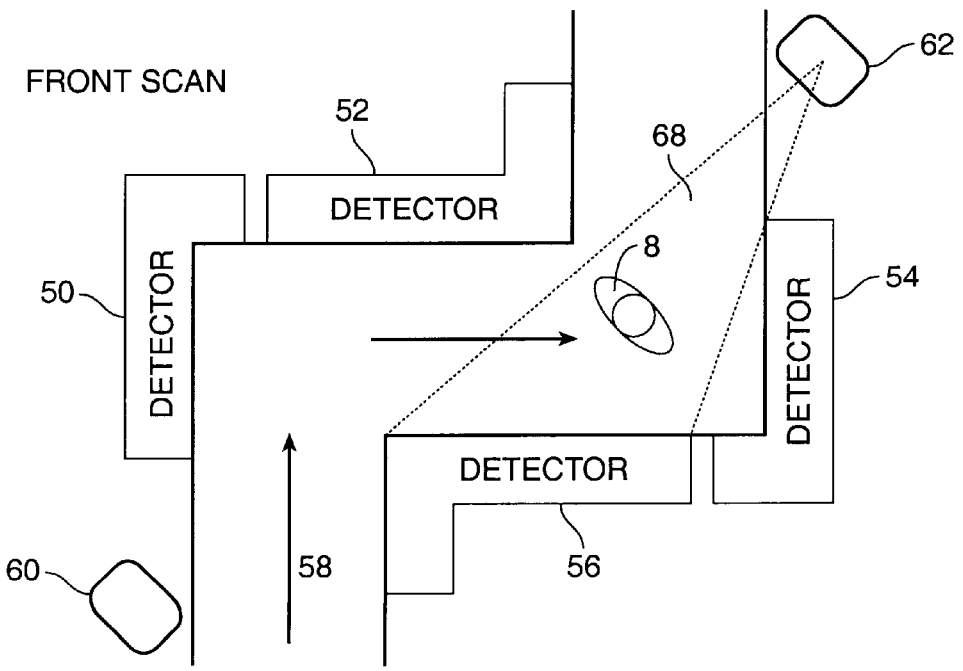

FIGS. 7a and 7b illustrates a second embodiment of the imaging system in which the portal structure is constructed in a zig-zag or double-L pattern having a right turn and a left turn. This configuration requires only two scan areas 62, 64. In a preferred second embodiment, the X-ray sources 60, 62 use a fast vertical sweep and slow horizontal sweep. A rear scan X-ray source 60 is positioned adjacent the portal entrance, and a front scan X-ray source 62 is located near the portal exit. As the subject 8 enters the portal along a direction of movement 58, the X-ray source 60 is activated. As the subject 8 begins to turn right at the first corner, the subject's back moves through a position that is perpendicular to the line of sight of the X-ray source 60. Backscatter detector 50 receives backscattered X-rays, and produces electrical signals that represent a rear scan of the subject. The portal and X-ray source configuration of the second embodiment does not provide true side views of the subject 8, and therefore, a transmission detector 52 is included to detect objects on the sides of the subject's body. As the subject 8 moves into scan area 68, the X-ray source 62 is activated, and produces X-rays which are directed towards the front side of the subject's body. Backscatter detector 54 collects backscattered X-rays, and transmission detector 56 collects X-rays that define an outline of the subject 8 for detecting objects on the sides of the subject's body. Because the X-rays of the backscatter imaging system are of a low level radiation which cannot penetrate the subject's body, the transmission detectors 52, 56 of this embodiment function only to produce an outline of the body. The outline image is formed from the X-rays which do not impinge upon and reflect off of the subject's body.

Figure 8A:
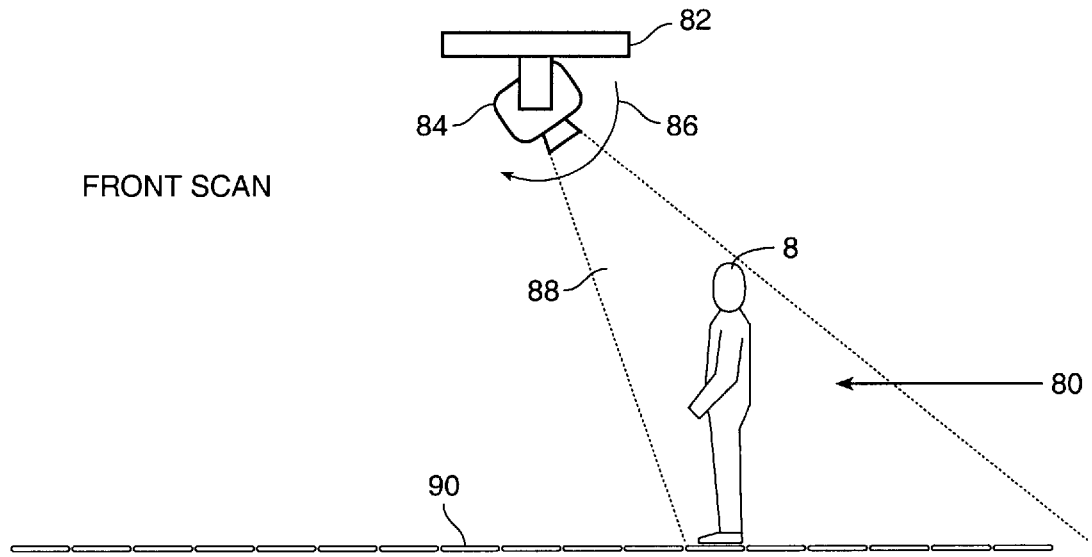
FIGS. 8a–8b illustrate a third embodiment of an X-ray imaging system, wherein a front scan of a subject is shown in FIG. 8a, and a rear scan of a subject is shown in FIG. 8b.
Figure 8B:
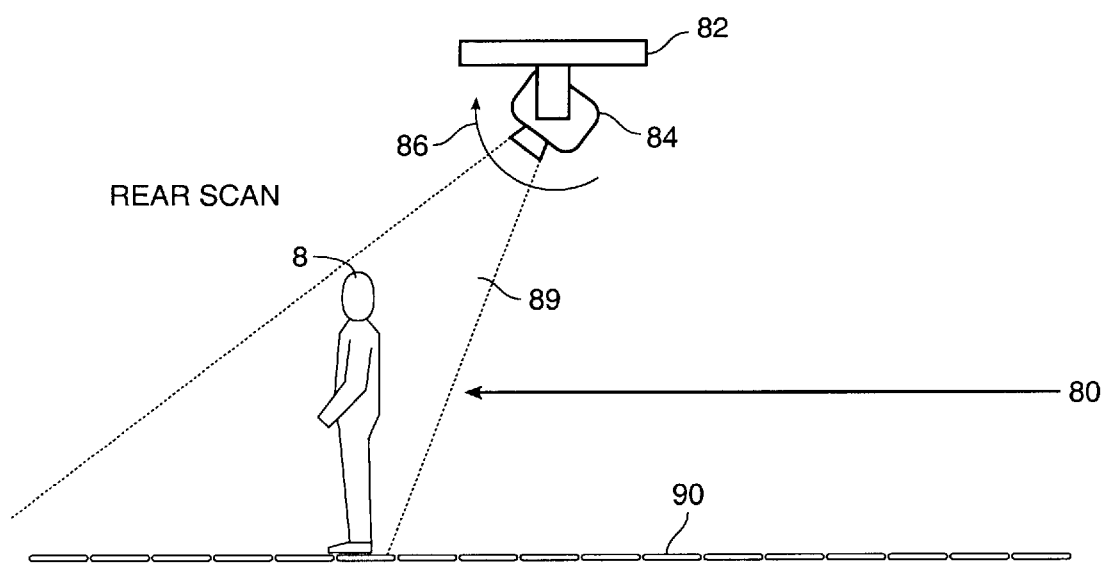

A third embodiment of the present invention, as illustrated in FIGS. 8a and 8b, employs an overhead X-ray source 84 which may be attached to an attachment structure 82. The X-ray source 84 rotates on an axis in an arc 86 which follows the direction of movement 80 of the subject 8. As the subject 8 moves into a front scan area 88 the X-ray source emits pencil beam X-rays in a horizontal plane which is directed downward. The rotation 86 of the X-ray source on the axis provides a vertical sweep of the front of the subject's body starting from the subject's head to the subject's feet. Scatter detectors and transmission detectors are located in the flooring 90 of the imaging system. The scatter detectors collect backscattered X-rays from the front of the subject's body, and the transmission detectors provide an outline scan of the subject to detect objects on the sides of the subject's body. Because the scan direction moves in the direction of the subject's movement, the image of the subject's body will appear to be compressed. As the subject 8 moves under and past the overhead X-ray source 84, he or she enters into an rear scan imaging area 89, and the X-ray source is rotating in a direction 86 which is now following the subject 8. Thus the X-ray source 84 will scan the rear of the subject 8 from foot to head. The forward motion of the subject 8 will result in a scanned image that appears stretched.

The fourth embodiment of the present invention, as illustrated in FIGS. 9a through 9e, utilizes a portal structure 100 similar to the preferred embodiment. Two stationary X-ray sources 102, 104 are mounted overhead in the ceiling of the portal structure 100. The chopper assemblies of the X-ray sources 102, 104 are configured to sweep beams 116, 114 in a horizontal plane. The X-ray sources 102, 104 are positioned so that the X-ray beams 116, 114 are directed downward to intersect the floor at a 45 degree angle. Vertical scanning of the subject 8 is achieved as the subject 8 moves forward through the slanted X-ray fan beam 116 as illustrated in the perspective view of FIG. 9e. As the subject 8 mover through the portal 7, the X-ray beam from X-ray source 102 provides the front scan, and the X-ray beam from X-ray source 104 provides the rear scan. The operation of sources 102, 104 is interlaced to avoid source interference.

Figure 9A:
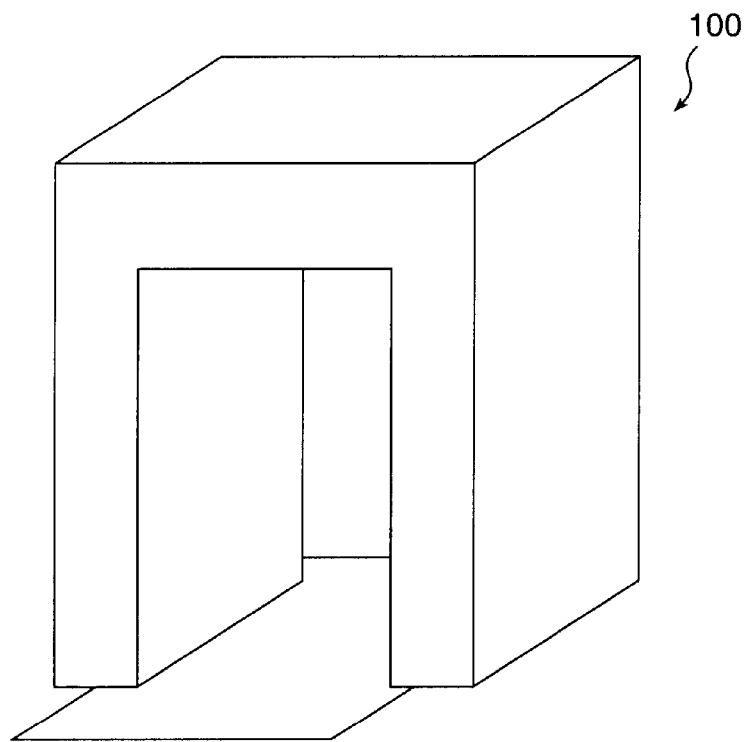
Figure 9B:
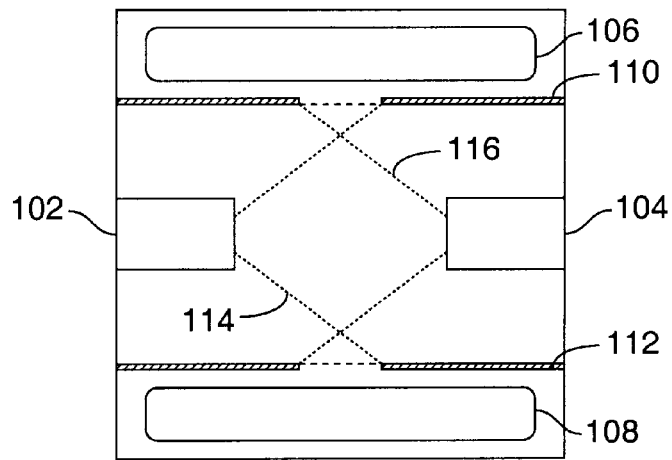
Figure 9C:
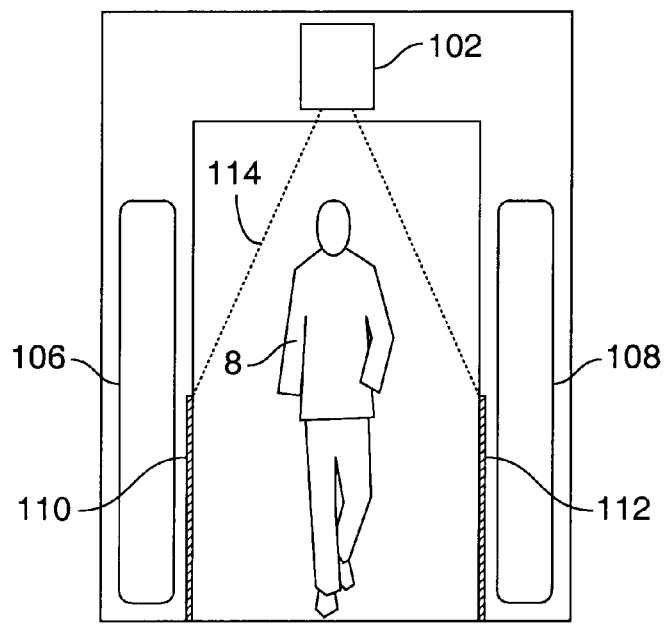
Figure 9D:
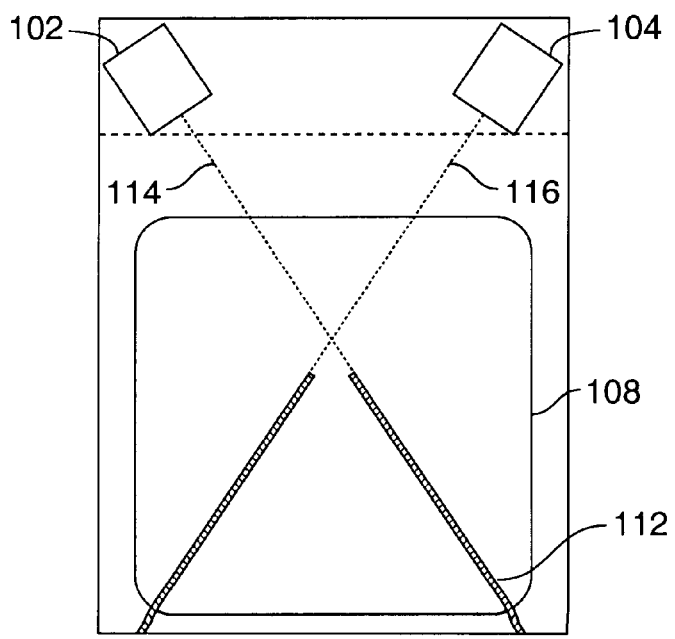
Figure 9E:
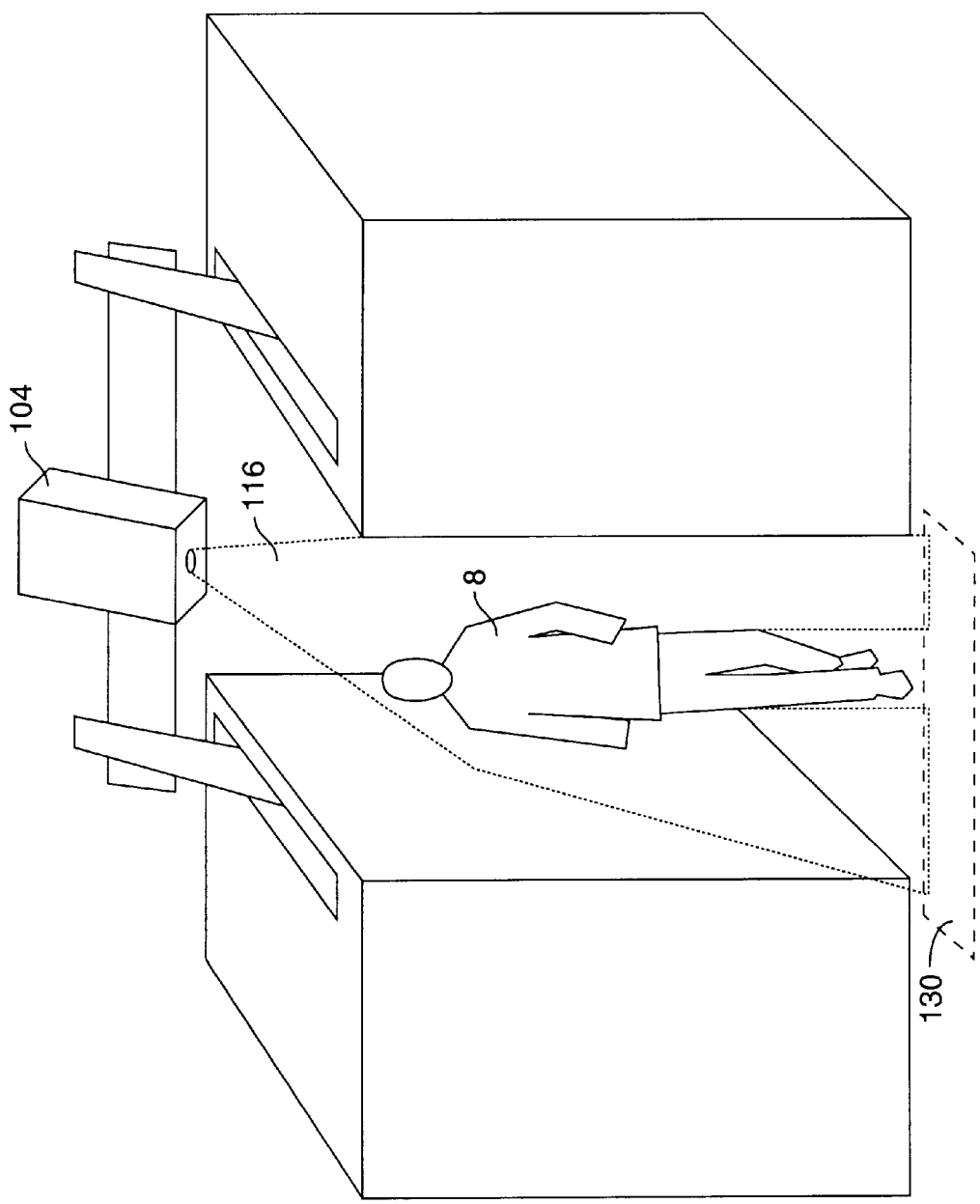

Scatter detectors 106, 108 are positioned to the left and to the right of the subject 8 to collect X-rays that are backscattered from the front side and the rear side of the subject's body. Transmission detectors 110, 112 are included in the configuration, and are positioned at an angle corresponding to the angle of the X-ray beams. Transmission detector 130 may also be located in the floor of the system as illustrated in FIG. 9e. The transmission detectors 110, 112 provide an outline scan of the subject's body to detect objects carried on the subject's side, which may not be detectable by the scatter detectors 106, 108.

While the invention has been particularly shown and described with reference to a preferred embodiment thereof, it will be understood by those skilled in the art that various changes in form and details may be made therein without departing from the spirit and scope of the invention.

I claim:

1. X-ray imaging apparatus for detecting an object carried by or on a body moving relative to the apparatus, said apparatus having an entrance and an exit, said apparatus comprising:
   a passageway extending at least from said entrance to said exit;
   at least one X-ray source having means for producing a pencil beam of X-rays directed toward said body in said passageway, said pencil beam intersecting said body at a region of intersection corresponding to a pixel having a pixel value;
   a scanning means disposed adjacent said at least one X-ray source for moving the region of intersection of said pencil beam and said body over a surface of said body;
   a tracking means for causing the scanning means to substantially track said body as it moves with respect to said apparatus from said entrance to said exit;
   a detector assembly for detecting an intensity of X-rays scattered from said body as a result of being scanned by said first scanning means and for generating a signal representative of the intensity of the scattered X-rays, said detector assembly comprising a plurality of detectors; and
   display means for presenting characteristics of the detector signal to an operator.

2. The X-ray imaging apparatus of claim 1, wherein said passageway comprises a left side and a right side relative to said body as said body moves between said left side and said right side of said passageway from said entrance to said exit, and wherein said at least one X-ray source comprises a first X-ray source disposed within said left side and a second X-ray source disposed within said right side.

3. The X-ray imaging apparatus as in claim 2, wherein said first X-ray source and said second X-ray source are disposed offset from each other along said passageway for scanning said subject from a plurality of angles.

4. The X-ray imaging apparatus as in claim 3, wherein said first X-ray source and said second X-ray source operate sequentially for providing a plurality of scans in a succession, said plurality of scans producing a plurality of images of said body at said plurality of angles.

5. The X-ray imaging apparatus of claim 4, wherein the plurality of images comprises four images.

6. The X-ray imaging apparatus of claim 2, wherein said plurality of detectors comprises a first array of detectors corresponding to said left side of said passageway and a second array of detectors corresponding to said right side of said passageway.

7. The X-ray imaging apparatus of claim 2, wherein said passageway further comprises a ceiling, wherein at least one detector of said plurality of detectors is disposed in said ceiling.

8. The X-ray imaging apparatus of claim 6, wherein said first X-ray source is disposed within said first array of detectors and said second X-ray source is disposed within said second array of detectors.

9. The X-ray imaging apparatus of claim 8, wherein each of said first X-ray source and said second X-ray source is disposed at a height generally corresponding to a mid-torso height of the body.

10. The X-ray imaging apparatus of claim 1, wherein each detector of said plurality of detectors comprises a fluorescent screen having a persistence of less that about 10 microseconds.

11. The X-ray imaging apparatus of claim 10, wherein said fluorescent screen is made from barium lead sulfate.

12. The X-ray imaging apparatus of claim 10, wherein said fluorescent screen is made from barium strontium sulfate.

13. The X-ray imaging apparatus of claim 1, wherein said tracking means comprises means for horizontally sweeping said scanning means.

14. The X-ray imaging apparatus of claim 13, wherein said means for horizontally sweeping comprises a turntable assembly for rotating said scanning means about a vertical axis.

15. The X-ray imaging apparatus of claim 13, wherein said means for horizontal sweeping comprises a horizontal axis disposed above said passageway, wherein said scanning means pivots on said horizontal axis.

16. The X-ray imaging apparatus of claim 13, wherein said means for horizontal sweeping comprises a horizontal beam disposed above said passageway and at least one slide means connected to said horizontal beam for sliding said scanning means within a horizontal plane.

17. The X-ray imaging apparatus of claim 1, wherein said at least one X-ray source comprises a first X-ray source and a second X-ray source, said first X-ray source and said second X-ray source each having a corresponding scanning means, wherein said tracking means comprises:
   a pair of offset mountings for mounting said first X-ray source and its corresponding first scanning means near said entrance and said second X-ray source and its corresponding first scanning means near said exit so that each of said first X-ray source and said second X-ray source is positioned to project said pencil beam substantially toward a longitudinal center portion of said passageway between said entrance and said exit; and
   a sequential timer for sequentially activating said first X-ray source and said second X-ray source as said body moves within said passageway.

18. The X-ray imaging apparatus of claim 17, wherein said passageway includes a plurality of turns therein.

19. The X-ray imaging apparatus of claim 1, wherein said at least one X-ray source comprises four X-ray sources, one X-ray source corresponding to one of four images.

20. The X-ray imaging apparatus of claim 19, wherein said tracking means comprises a timing device for sequentially activating said four X-ray sources one at a time as the body progresses through the passageway.

21. The X-ray imaging apparatus of claim 1, wherein said scanning means comprises a chopper assembly for vertically translating said pencil beam over a length of said body.

22. The X-ray imaging apparatus as in claim 21, wherein said scanning means further comprises a means for horizontally moving said pencil beam over a width of said body.

23. The X-ray imaging apparatus of claim 1, further comprising at least one sensor for sensing movement of said body with respect to said apparatus and generating a motion signal in response thereto.

24. The X-ray imaging apparatus of claim 23, wherein said tracking means is responsive to said motion signal.

25. The X-ray imaging apparatus of claim 1, further comprising a mechanical means for moving said body through said passageway.

26. The X-ray imaging apparatus of claim 25, wherein the mechanical means for moving said body comprises a moving walkway.

27. The X-ray imaging apparatus of claim 1, wherein said at least one X-ray source comprises an X-ray tube operating at a potential of 70 KV at 10 ma.

28. The X-ray imaging apparatus of claim 1, wherein each pixel has an area on the order of 15 square millimeters.

29. In an X-ray backscatter imaging system for searching a subject for concealed objects, a method comprising the steps of:

moving the subject within a passageway, the passageway having an entrance and an exit;

initiating operation of at least one X-ray source upon entry of the subject into the passageway;

producing a pencil beam of X-rays having a low dose directed toward a scanning area at a plurality of scanning positions within the passageway;

scanning the pencil beam of X-rays over the scanning area;

tracking said pencil beam of X-rays to each of said plurality of scanning positions, wherein the tracking is substantially coordinated with forward progress of the subject through the passageway;

using a plurality of detectors, detecting X-rays that are backscattered from said pencil beam as a result of interacting with the subject when positioned at each scanning position of the plurality of scanning positions; and displaying a digitally represented image of the detected backscattered X-rays.

30. The method of claim 29, wherein said step of scanning comprises chopping the pencil beam of X-rays using a rotating chopper.

31. The method of claim 30, wherein the step of tracking comprises rotating an X-ray source and the rotating chopper on a turntable disposed at a side of the passageway.

32. The method of claim 29, wherein the step of tracking comprises pivoting an X-ray source and the rotating chopper on a horizontal axis disposed above the passageway.

33. The method of claim 29, wherein the step of tracking is coordinated with the movement of the subject by sequentially activating a plurality of X-ray sources, each X-ray source generating a different vertically-scanned pencil beam of X-rays.

34. The method of claim 33, wherein the plurality of X-ray sources comprises two X-ray sources disposed on opposite sides of the passageway.

35. The method of claim 34, wherein the step of sequentially activating the two X-ray sources includes separately activating each X-ray source as the subject approaches a longitudinal center of the passageway and as the subject moves away from the longitudinal center of the passageway so that four scanning positions are defined.

36. The method of claim 33, wherein the plurality of X-ray sources comprises two X-ray sources disposed on opposite ends of the passageway.

37. The method of claim 36, wherein the step of sequentially activating the two X-ray sources includes separately activating a first X-ray source as the subject approaches a longitudinal center of the passageway and a second X-ray source as the subject moves away from the longitudinal center of the passageway so that at least two scanning positions are defined.

38. The method of claim 29, wherein the plurality of detectors comprises detector arrays, one detector array disposed in opposite sides of the passageway.

39. The method of claim 29, further comprising sensing a presence of the subject at an entrance of the passageway and generating an initiation signal to the imaging system.

40. An X-ray imaging system for detecting an object carried by or on a body, said system having an entrance and an exit, said system comprising:

a passageway extending from said entrance to said exit;

at least one X-ray source for producing a pencil beam of X rays directed toward said body in said passageway, said at least one X-ray source comprising a collimator mechanism for scanning said pencil beam in a parallel beam plane;

a scanning assembly for scanning said parallel beam plane over a surface of said body as said body moves in a direction of movement from said entrance to said exit;

a tracking assembly for causing said scanning assembly to substantially track said body as it moves with respect to said system from said entrance to said exit;

a detector array for detecting an intensity of X-rays scattered from said body and for generating a detector signal representative of an intensity of said scattered X-rays, said detector array comprising at least one detector; and a processor assembly for presenting characteristics of said detector signal to an operator, and for controlling said X-ray source, said scanning assembly, said tracking assembly, and said detector array.

41. The X-ray imaging system of claim 40, wherein said passageway comprises a left side and a right side with respect to said body as said body moves through said passageway, and wherein said at least one X-ray source comprises a first X-ray source disposed within said left side and a second X-ray source disposed within said right side.

42. The X-ray imaging system as in claim 41, wherein said first X-ray source and said second X-ray source are disposed offset from each other along said passageway for scanning said subject from a plurality of angles.

43. The X-ray imaging system as in claim 42, wherein said first X-ray source and said second X-ray source operate sequentially for providing a plurality of scans in a succession, said plurality of scans producing a plurality of images of said body at said plurality of angles.

44. The X-ray imaging system of claim 43, wherein said plurality of images comprises a left front image, a left rear image, a right front image, and a right rear image of said body.

45. The X-ray imaging system of claim 41, wherein said detector array comprises a first array of detectors corresponding to said left side of said passageway and a second array of detectors corresponding to said right side of said passageway.

46. The X-ray imaging system of claim 45, wherein said passageway further comprises a ceiling.

47. The X-ray imaging system of claim 46, wherein said detector array further comprises at least one ceiling detector disposed in said ceiling.

48. The X-ray imaging system of claim 40, wherein said at least one detector comprises a fluorescent screen having a persistence of less that about 10 microseconds.

49. The X-ray imaging system of claim 48, wherein said fluorescent screen is made from barium lead sulfate.

50. The X-ray imaging system of claim 48, wherein said fluorescent screen is made from barium strontium sulfate.

51. The X-ray imaging system of claim 40, wherein said parallel beam plane is a vertical beam plane over a length of said body.

52. The X-ray imaging system as in claim 51, wherein said scanning assembly horizontally sweeps said vertical beam plane over a width of said body.

53. The X-ray imaging system of claim 52, wherein said tracking assembly comprises a turntable assembly for rotating said vertical beam plane about a vertical axis.

54. The X-ray imaging system of claim 40, wherein said at least one X-ray source comprises an overhead X-ray source disposed above said passageway.

55. The X-ray imaging system of claim 54, wherein said tracking assembly causes said scanning assembly to pivot said parallel beam plane about a horizontal axis, said parallel beam plane tracking said body along to said direction of movement.

56. The X-ray imaging system of claim 40, wherein said passageway includes a plurality of turns therein.

57. The X-ray imaging system of claim 40, wherein said at least one X-ray source comprises four X-ray sources, one X-ray source corresponding to one of four images.

58. The X-ray imaging system of claim 57, further comprising a timing device for sequentially activating said four X-ray sources one at a time as said body progresses through said passageway.

59. The X-ray imaging system of claim 40, further comprising at least one sensor for sensing movement of said body with respect to said system and for generating a motion signal in response thereto.

60. The X-ray imaging system of claim 59, wherein said processor assembly utilizes said motion signal for controlling said X-ray imaging system.

61. The X-ray imaging system of claim 40, further comprising a mechanical assembly for moving said body through said passageway.

62. The X-ray imaging system of claim 61, wherein said mechanical assembly for moving said body comprises a moving walkway.

63. The X-ray imaging system of claim 40, wherein said at least one X-ray source comprises an X-ray tube operating at a potential of 70 KV at 10 ma.

64. The X-ray imaging system of claim 40, wherein said pencil beam has a cross-sectional area corresponding to a pixel a point where said pencil beam intersects said body, said pixel having an area on the order of 15 square millimeters.

65. The X-ray imaging system of claim 40, wherein said processor assembly comprises a monitor screen for displaying an image representative of said body.

66. The X-ray imaging system of claim 40, wherein said detector array further comprises at least one transmission detector.

67. An apparatus for detecting an object carried by or on a body, said apparatus comprising:

a flooring having a length, said body moving across said flooring in a direction of movement;

at least one X-ray source positioned above said flooring and at a height sufficient to allow said body to pass below said at least one X-ray source, said at least one X-ray source emitting an X-ray pencil beam scanned in a horizontal plane to produce a horizontal beam plane, said horizontal beam plane directed toward said body;

a tracking assembly for rotating said horizontal beam plane through a tracking angle and in a direction corresponding to said direction of movement, wherein a starting portion of said tracking angle directs said horizontal beam plane to a front area of said body, and an ending portion of said tracking angle directs said horizontal beam plane to a back area of said body;

a detector array disposed in said flooring and positioned along said length, said detector array comprising at least one scatter detector for detecting an intensity of X-rays scattered from said body and for generating a detector signal representative of the intensity of the scattered X-rays; and a processor assembly for controlling said apparatus, said processor comprising an interface for presenting a representation of said detector signal to an apparatus operator.

68. The apparatus as in claim 67, wherein said detector array further comprises at least one transmission detector disposed adjacent said at least one scatter detector.

69. The apparatus as in claim 68, wherein said at least one scatter detector comprises a plurality of scatter detectors, and said at least one transmission detector comprising a plurality of transmission detectors, wherein said plurality of transmission detectors is dispersed among said plurality of scatter detectors.

70. The apparatus as in claim 67, further comprising at least one sensor for sensing movement of said body along said length of said flooring and for generating a motion signal in response thereto.

71. The apparatus as in claim 70, wherein said processor assembly utilizes said motion signal for controlling said at least one X-ray source and said tracking assembly.

72. The apparatus as in claim 67, wherein said flooring further comprises a mechanical assembly for moving said body in said direction of movement.

73. The apparatus as in claim 72, wherein said mechanical assembly for moving said body comprises a moving walkway.

74. An X-ray imaging system for detecting concealed objects on a body, said body having a body front, a body back, and body sides, said system comprising:

a portal structure comprising a first side module, a second side module, and a ceiling module, said first side module and said second side module parallel and separated by a portal width, said ceiling module positioned above said first side module and said second side module to form a portal having an entrance and an exit;

a detector array for producing a detector signal from scattered X-rays, said detector array having a first side detector array concealed within said first side module and a second side detector array concealed within said second side module;

an X-ray source for emitting a pencil beam of X-rays scanned across a scanning plane, said X-ray source concealed within said ceiling module, said scanning plane directed toward said exit and at a downward angle;

a tracking assembly for rotating said scanning plane through a tracking angle and in a direction progressing from said entrance to said exit to substantially track said body as it moves with respect to said system from said entrance to said exit; and a display means for presenting characteristics of said detector signal;

wherein said body moves through said scanning plane as said body moves from said entrance to said exit, said pencil beam of X-rays of said scanning plane striking said body front and producing said scattered X-rays.

75. The X-ray imaging system as in claim 74, wherein said downward angle is a 45 degree angle.

76. The X-ray imaging system as in claim 74, further comprising a second X-ray source for emitting a second pencil beam of X-rays scanned across a second scanning plane, said second X-ray source located in said ceiling and directed toward said entrance at a second downward angle, wherein said scanning plane strikes said body back as said body moves from said entrance to said exit.

77. The X-ray imaging system as in claim 76, wherein said second downward angle is a 45 degree angle.

78. The X-ray imaging system as in claim 76, wherein said X-ray source and said second X-ray source alternately emit said first scanning plane and said second scanning plane.

79. The X-ray imaging system as in claim 74, further comprising a first transmission detector located in said first side module, and a second transmission detector located in said second side module, said first and second transmission detectors for detecting transmitted X-rays, and for producing a transmission detector signal for detecting said concealed objects on said body sides.

80. The X-ray imaging system as in claim 79, wherein said first and second transmission detectors are positioned at said downward angle.

81. The X-ray imaging system as in claim 76, further comprising a plurality of transmission detectors for detecting transmitted X-rays, and for producing a transmission detector signal for detecting said concealed objects on said body sides.

82. The X-ray imaging system as in claim 81, wherein a first and second transmission detector of said plurality of transmission detectors is located in said first side module and said second side module respectively, and wherein said first and second transmission detectors are positioned at said downward angle.

83. The X-ray imaging system as in claim 82, wherein a third and fourth transmission detector of said plurality of transmission detectors is located in said first side module and said second side module respectively, and wherein said third and fourth transmission detectors are positioned at said second downward angle.

* * * * *

UNITED STATES PATENT AND TRADEMARK OFFICE
CERTIFICATE OF CORRECTION

PATENT NO. : 6,094,472
DATED : July 25, 2000
INVENTOR(S) : Steven W. Smith

It is certified that error appears in the above-identified patent and that said Letters Patent is hereby corrected as shown below:

<u>Title page,</u>
ABSTRACT, after "exit" insert -- . --.

<u>Column 4,</u>
Line 1, replace "an" with -- a --.

<u>Column 5,</u>
Line 51, replace "5c" with -- 6c --.
Line 52, replace "5d" with -- 6d --.

<u>Column 7,</u>
Line 43, replace "12,14,  15." with -- 12, 14, 15. --.

<u>Column 10,</u>
Line 50, replace "an" with -- a --.

<u>Column 11,</u>
Line 1, replace "mover" with -- moves --.

<u>Column 12,</u>
Line 18, replace "that" with -- than --.

<u>Column 15,</u>
Line 6, replace "that" with -- than --.

Signed and Sealed this

Twelfth Day of March, 2002

*Attest:*

*Attesting Officer*

JAMES E. ROGAN
*Director of the United States Patent and Trademark Office*